United States Patent
Kaps et al.

(10) Patent No.: US 8,734,828 B2
(45) Date of Patent: May 27, 2014

(54) MATRIX-GEL GRAFT WITHOUT CELLS

(75) Inventors: Christian Kaps, Berlin (DE); Eszter Tanczos, Kuesnacht (CH)

(73) Assignee: BioTissue AG, Zurich (CH)

(*) Notice: Subject to any disclaimer, the term of this patent is extended or adjusted under 35 U.S.C. 154(b) by 625 days.

(21) Appl. No.: 12/418,942

(22) Filed: Apr. 6, 2009

(65) Prior Publication Data

US 2009/0252798 A1   Oct. 8, 2009

Related U.S. Application Data

(63) Continuation of application No. PCT/EP2007/060384, filed on Oct. 1, 2007.

(30) Foreign Application Priority Data

Oct. 6, 2006 (DE) .................. 10 2006 047 346

(51) Int. Cl.
*A61F 2/00* (2006.01)
*A61K 9/14* (2006.01)

(52) U.S. Cl.
USPC ......................................... 424/423; 424/486

(58) Field of Classification Search
None
See application file for complete search history.

(56) References Cited

U.S. PATENT DOCUMENTS

| | | | |
|---|---|---|---|
| 4,582,865 A * | 4/1986 | Balazs et al. ................ | 524/29 |
| 4,813,967 A | 3/1989 | Renard et al. | |
| 4,828,563 A | 5/1989 | Mueller-Lierheim | |
| 5,891,455 A | 4/1999 | Sittinger et al. | |
| 5,932,459 A | 8/1999 | Sittinger et al. | |
| 6,506,217 B1 | 1/2003 | Arnett | |
| 6,602,294 B1 | 8/2003 | Sittinger et al. | |
| 6,872,819 B1 * | 3/2005 | Pavesio et al. ............... | 536/55.3 |
| 2002/0052044 A1 | 5/2002 | Jeschke et al. | |
| 2002/0119179 A1 | 8/2002 | Rezania et al. | |
| 2003/0003153 A1 | 1/2003 | Asculai et al. | |
| 2003/0031695 A1 | 2/2003 | Kadiyala et al. | |
| 2004/0076656 A1 | 4/2004 | Pavesio et al. | |
| 2004/0241144 A1 | 12/2004 | Kaps et al. | |
| 2004/0267362 A1 | 12/2004 | Hwang et al. | |
| 2005/0043814 A1 | 2/2005 | Kusanagi et al. | |
| 2005/0147642 A1* | 7/2005 | Laredo et al. ................ | 424/423 |
| 2005/0283224 A1* | 12/2005 | King ........................... | 623/1.13 |
| 2006/0241756 A1 | 10/2006 | Fritz et al. | |
| 2007/0020230 A1 | 1/2007 | Kaps et al. | |
| 2008/0206302 A1 | 8/2008 | Sittinger et al. | |
| 2008/0260801 A1 | 10/2008 | Ahlers et al. | |
| 2009/0017093 A1 | 1/2009 | Springer et al. | |

FOREIGN PATENT DOCUMENTS

| | | |
|---|---|---|
| CA | 2 629 794 | 5/2007 |
| DE | 4306661 | 9/1994 |
| DE | 4431598 | 3/1996 |
| DE | 199 57 388 A1 | 6/2001 |
| DE | 19957388 | 6/2001 |
| DE | 100 06 822 | 8/2001 |
| DE | 10042484 | 3/2002 |
| DE | 10139783 | 4/2003 |
| DE | 10333901 | 3/2005 |
| DE | 103 48 219 A1 | 5/2005 |
| DE | 102005034420 | 7/2006 |
| DE | 10 2005 030 614 | 1/2007 |
| DE | 10 2005 054 940 A1 | 1/2007 |
| EP | 1 273 312 | 1/2003 |
| EP | 1273312 * | 1/2003 |
| EP | 1 410 811 A1 | 4/2004 |
| GB | 1052589 | 12/1966 |
| JP | 61-502448 | 10/1986 |
| JP | 62-49856 | 3/1987 |
| WO | WO 94/14390 | 7/1994 |
| WO | 9715655 | 5/1997 |
| WO | 01/54735 | 8/2001 |
| WO | 01-54735 | 8/2001 |
| WO | 0166130 | 9/2001 |
| WO | 0200272 | 1/2002 |
| WO | 0238163 | 5/2002 |
| WO | 2005/014027 | 2/2005 |
| WO | 2006-104901 | 10/2006 |
| WO | WO2006104901 * | 10/2006 |
| WO | 2007/003324 | 1/2007 |

OTHER PUBLICATIONS

Shu et al. (2004) Biomaterials 25; 1339-1348.*
Lee et al. (2003) Biomaterials 24, pp. 5049-5059.*
Liu et al. (2007) J. Biomaterials Applications vol. 21 pp. 413-430.*
Shu et al. (2003) Biomaterials 24, pp. 3825-3834.*
Australian Office Action mailed Mar. 31, 2010, in Australian patent application No. 2007304237.
Encyclopedia Britannica Online (serum and plasma), Jun. 5, 2011.
Office Action issued Feb. 15, 2011, in Japanese Patent Application No. 2008-514034, which was filed on Nov. 30, 2007.
Michel J. J. Hooiveld, et al., "Immature Articular Cartilage is More Susceptible to Blood-Induced Damage Than Mature Articular Cartilage", Arthritis & Rheumatism, vol. 48, No. 2, Feb. 2003, pp. 396-403.
Michel J. J. Hooiveld, et al., "Haemoglobin-Derived Iron-Dependent Hydroxyl Radical Formation in Blood-Induced Joint Damage: An In Vitro Study", Rheumatology 2003;42:784-790.

* cited by examiner

*Primary Examiner* — Chris R Tate
*Assistant Examiner* — Russell Fiebig
(74) *Attorney, Agent, or Firm* — Oblon, Spivak, McClelland, Maier & Neustadt, L.L.P.

(57) ABSTRACT

A cell-free graft contains (i) a cohesive, scaffold-forming matrix with open porosity containing a biologically and pharmaceutically acceptable material, and (ii) a gel of a biologically and pharmaceutically acceptable material. The cell-free graft is produced by (v) contacting the matrix with the gel, and (vi) drying the matrix-gel complex formed in (v). The cell-free graft can be used for covering and increasing the viscoelasticity of defects, for tissue regeneration and in particular for regenerating mesenchymal tissue, especially cartilage and/or bone.

14 Claims, 3 Drawing Sheets

MATRIX-GEL GRAFT WITHOUT CELLS

BACKGROUND OF THE INVENTION

1. Field of the Invention

The present invention relates to a cell-free matrix-gel graft for tissue regeneration and, in particular, for cartilage regeneration, a method for its production and the use of the graft for tissue regeneration.

2. Discussion of the Background

The articular cartilage is indispensable as sliding surface for normal joint function. Damage to the articular cartilage occurs for example in osteoarthrosis, trauma or osteochondritis dissecans. The articular cartilage cells of which the articular cartilage is composed have only low regeneration ability in adults.

The articular cartilage is a mesodermal tissue type which is derived from connective tissue and which can be ascribed to multipotent, undifferentiated mesenchymal progenitor cells. Hyaline cartilage is the most widespread type of cartilage and is found for example in the joint surfaces. Cartilage defects owing to wear or damage represent a widespread medical problem. For this reason, in the past, especially in recent years, methods and techniques have been developed for replacing defective chondral or else osteochondral areas in the articular cartilage. Thus, periosteal, perichondral, allogeneic and autologous osteochondral grafts, allogeneic menisci or else prostheses made of synthetic materials have been employed as replacement for articular cartilage.

In the autologous grafting of chondrocytes, chondrocytes taken from the patient are expanded in cell culture and returned to the patient. A wide variety of types of graft is possible for the return. Examples thereof are injection solutions injected into the joint, matrices inoculated with cartilage cells, and the like.

For example, WO 97/15655 describes artificial tissues consisting of three-dimensional extracellular matrices and genetically manipulated cells, where the matrices are able to release immunosuppressive or cell-differentiating factors. The matrices are preferably in the form of a polymer web into which a cell suspension, which may for example be suspended in a fibrinogen solution, is dispersed. It is additionally possible to add to the matrix factors or components of the appropriate extracellular matrix which promote the growth and/or differentiation process. In order to keep the cells in the matrix, the cell suspension can be consolidated by adding thrombin in order to obtain the finished graft.

DE 44 31 598 describes a method for producing an implant from cell cultures, in which three-dimensional support structures on which cells are deposited are initially enveloped and then perfused with a nutrient solution. Absorbable microparticles are incorporated into the support structures and release factors which influence tissue formation during absorption.

DE 100 06 822 describes a method for producing a bone or cartilage graft in which bioabsorbable and biocompatible framework structures consist of osteogenic cells crosslinked by fibrin or hydrogel, and factors, and have been shaped to geometric articles which can be fitted together.

DE 43 06 661 describes a three-dimensional support structure, preferably made of a polymer web, into which cells are incorporated. The support structure is then perfused in nutrient solution in order to promote cell growth and the formation of an extracellular matrix by the cells. The support structure is enveloped with agarose in order to prevent the cells migrating out or being washed out.

DE 101 39 783 further discloses the provision of mesenchymal cells in synovial fluid. This composition can, if desired, also be applied to a support such as a web or a synthetic material and be used in this form as graft. Otherwise, the suspension of cells in synovial fluid is injected as such into the affected joint.

Alternatively, matrix structures which themselves do not contain any cells are synthesized. Thus, for example, US 2003/0003153 describes reinforced matrix membranes which comprise one or more scaffold-forming proteins which are suitable for cell growth. It is assumed in these cases that cells from endogenous tissue will migrate into the matrix structure. This is achieved for example by conventional Pridie perforation or microfracturing. In these techniques, slight perforations or fractures are introduced into the bone of the joint as far as the bone marrow. Bleeding occurs through the perforations into the defect, thus filling the defect with a blood clot. Mesenchymal progenitor cells are present in the clot and, when stimulated by appropriate stimuli, are able to form a cartilage-like replacement tissue, called fibrous cartilage. If a matrix material is provided over the Pridie perforation, the blood cells are able to migrate into this matrix material and settle there.

DE 199 57 388 and WO 2005/014027 make use of this effect and enhance it by providing growth and differentiation factors (DE 199 57 388), chemokines (WO 2005/014027) or blood serum (DE 10 2005 030 614) as recruiting agents in the matrix structure. All the factors are intended to lead to enhanced recruitment of the cartilage-forming mesenchymal progenitor cells, the ultimate intention being to achieve faster regeneration of the cartilage.

WO 02/00272, finally, discloses the possibility of producing corresponding grafts also from blood and a polymer component. This document addresses the problem that the blood clot normally produced in the Pridie perforation contracts on coagulation and thus changes shape. The added polymer prevents this change in shape and thus permits true-shape healing. The graft is produced by a polymer being mixed with blood or a blood component such as erythrocytes, leukocytes, monocytes, platelets, fibrinogen, thrombin and platelet-rich plasma and being introduced into the defect. However, when a blood component is used it is essential that material capable of coagulation is present in order to achieve the desired effect.

US2005/0043814 finally discloses a cell-free matrix implant with optional bone-inducing composition, which includes a collagenous, thermo-reversible gel, an aromatic organic acid or an adsorbable caprolactone polymer support matrix. The bone-inducing composition may comprise polyglycolic acid polymers and be applied to a matrix of collagens or polyglycolic acids. When this cell-free matrix implant is used, it is essential that the gel is thermo-reversible because this makes it possible for the composition to be applied in liquid form. Only after injection of the liquid composition does it solidify in the patient's body.

The disadvantages of the technologies described above are that if the graft itself comprises cells, these are frequently damaged by the manipulation during handling, the graft has to be produced by a lengthy culturing method on use of cells, especially autologous cells, and requires careful checks on contamination, and finally storability is lacking, or storage is possible only under complicated conditions.

These disadvantages are further enhanced on use of allogeneic, exogenous cells to the extent that an elaborate bacteriological and virological investigation of the donor cells is necessary in order to avoid transmission of diseases by the cell-containing graft. In addition there is the danger of a rejection response on use of exogenous cells.

Further disadvantages of the technologies described above are that factors which accelerate or enable the migration in of cells are added to cell-free grafts. These factors may be for example either growth and differentiation factors or chemokines. These factors are of animal origin, i.e. isolated from animals, or are produced recombinantly by bacteria or yeasts. However, the factors produced on recombinant production are predominantly derived from a structure of animal origin. This is disadvantageous because, owing to the difference between "donor" and "recipient" of these constituents of the graft, it is easily possible for incompatibilities or allergic reactions to occur after the grafting.

The use of blood, blood components or serum for recruiting cells into the cell-free graft is inadequate in as much as elaborate bacteriological and virological investigations are likewise necessary on use of allogeneic, exogenous blood to avoid transmission of diseases. On the other hand, a precondition for the use of endogenous blood, blood components or serum is additional manipulation on the graft (introduction of the component) and on the patient (taking of blood). Every manipulation on the graft entails the risk of contamination of the graft, which may likewise lead to incompatibility in the patent. In addition, the additional removal of material from the patient necessary for this is associated with undesirably long times required and additional costs.

The disadvantage of the use of implants which solidify after implantation is that a solid, set implant mechanically damages the surrounding tissue of lower strength/hardness. In addition, a solid implant impedes the migration in of cells and requires very long break-down times and absorption times.

A further disadvantage of the cell-free grafts described above is that in the background art they are employed after a Pridie perforation or microfracturing in order to accommodate nonselectively all the cells which have been introduced or imported during the bleeding into the cell-free graft. This may result in overgrowth of the graft with cells and/or constituents not typical of the tissue, which might impede the formation of the desired tissue or promote the formation of a mixed tissue. Such a bleeding into the defect is disadvantageous in as much as it may lead to irritation and inflammation of the surrounding tissue. Thus, Hooiveld and colleagues describe damage to cartilage cells resulting from bringing cartilage together with blood or blood components for 4 days [Hooiveld M. J. et al.: Haemoglobin-derived iron-dependent hydroxyl radical formation in blood-induced joint damage: an in vitro study, Rheumatology 43, 784-790, 2003]. Hooiveld further describes the possibility of internal synovial membrane inflammation (synovitis) being caused by bleeding into the joint [Hooiveld M. J. et al.: Immature articular cartilage is more susceptible to blood-induced damage than mature articular cartilage: an in vivo animal study, Arthritis Rheum 48, 396-403, 2003].

It is particularly disadvantageous with the grafts known in the background art that, because of the cells or biological constituents present, they can be stored for only a very limited time and additionally require very specific storage conditions.

The present invention has the object inter alia of providing a graft which is simple to produce, requires the minimum number of manipulation steps for production and can be stored very easily. It was additionally intended that it can be used rapidly and simply, but nevertheless ensure comparable and/or at least as good therapeutic results as the grafts known in the background art. It would further be desirable to be able to dispense as far as possible with the use of exogenous, where appropriate even recombinant growth factors, which potentially represent allergens. It would also be desirable to be able as far as possible to dispense with additional removal of blood or the use of blood, blood components or serum, because this represents an additional risk of contamination and stress for the patient. It would further be desirable to be able to prevent as far as possible the bleeding into the defect after Pridie perforation or microfracturing, in order to be able to avoid damage to the surrounding articular tissue. It would also be desirable for the cell-free graft to have the strength or elasticity of the surrounding tissue, in order to prevent mechanical damage to the surrounding tissue. In this context a possible adaptation of the hardness/elasticity of the graft to the individual patent in order to minimize unharmonic movements caused by different hardnesses of the materials would be desirable.

SUMMARY OF THE INVENTION

The present invention solves the background art problems. For this purpose, it provides a matrix-gel graft, comprising:
(i) a cohesive, scaffold-forming matrix with open porosity comprising a biologically and pharmaceutically acceptable material; and
(ii) a gel of a biologically and pharmaceutically acceptable material.

In a second aspect, a method for producing such a cell-free matrix-gel graft is provided, comprising:
(v) contacting the matrix with the gel, and
(vi) drying the matrix-gel complex formed in (v).

In a third aspect, the present invention provides the use of the cell-free matrix-gel graft for covering and increasing the viscoelasticity of defects, for tissue regeneration and, in particular, for regenerating mesenchymal tissue, especially of cartilage and/or bone.

DETAILED DESCRIPTION OF THE INVENTION

Figure 1:
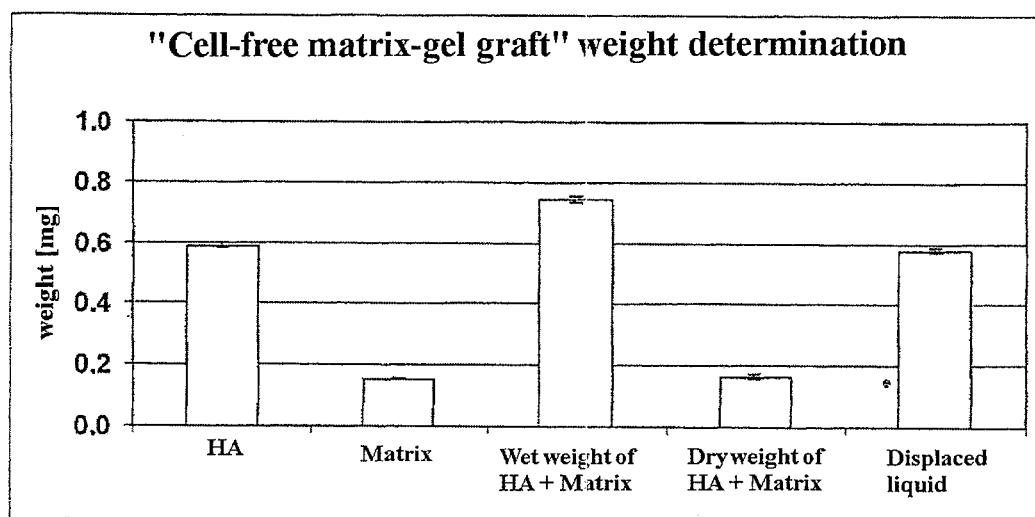
FIG. 1 shows the respective weight of a cell-free graft before and after drying by lyophilization, and the weight of the displaced liquid. The abbreviations in this case mean "HA" hyaluronic acid and "mg" milligrams. The exact design of the experiment underlying this figure is described in example 1.

The present invention relates to a cell-free implant, comprising:
(i) a cohesive, scaffold-forming matrix with open porosity comprising a biologically and pharmaceutically acceptable material; and
(ii) a gel of a biologically and pharmaceutically acceptable material.

The matrix of the cell-free graft of the invention is a cohesive, scaffold-forming matrix with open porosity. The expression "cohesive" means herein that the matrix allows the graft to be handled without thereby disintegrating into individual parts or constituents. It is unnecessary for all the constituents of the matrix to be linked together by chemical bonds or interactions. A mechanical connection by, for example, weaving, milling, twisting or the like is sufficient.

The expression "scaffold-forming" means herewith the property of the matrix acting as structure former for the tissue matrix to be produced from the cells which have migrated in. The matrix additionally forms a scaffold or lattice in which the cells can settle and be held in order not to be flushed out of the matrix for example by synovial fluid or blood.

"Open porosity" finally means in the context of the invention that the spaces between the scaffold structures of the matrix are accessible for material and in particular fluid exchange with the surroundings of the matrix. The pore size of the pores is preferably such that it is also possible for cells to penetrate in and be rinsed. However, open porosity in the context of the invention also means a structure like that present in gels. In this case, the skeleton of the gel former provides the scaffold structures of the matrix. Between these there are hydration sheaths and fluid into which cells can penetrate and with which fluid exchange is possible. Corresponding gel structures are therefore also understood to be matrices with open porosity within the meaning of the present invention.

The scaffold structures with open porosity are preferably selected from woven or unwoven fabrics (knits), in particular nonwoven and felt structures, membranes, sponges, wadding, open-cell foams, wool, braids, ordered and unordered fiber bundles, porous ceramic materials, spongiosa and gels, and combinations thereof. The matrix preferably has a nonwoven or felt structure. Combinations of various structures, for example in layered arrangement, are possible and within the scope of the present invention.

The matrix material may in principle be any suitable, biologically and pharmaceutically acceptable material. The matrix material used in the matrix of the invention may be absorbable or non-absorbable. Absorbable materials are preferred. The matrix preferably includes a material selected from the group consisting of natural and synthetic polymers such as collagen, hyaluronic acid, chitosan, chitin, polysaccharides, celluloses and derivatives thereof, proteins, polypeptides, polyglycolic acid, polylactic acid, poly(glycolide, lactate), caprolactone and mixtures thereof. Very particular preference is given to polyglycolic acid (PGA), polylactic acid, collagen or hyaluronic acid.

Polyglycolic acids preferably used are pure polyglycolic acids having molecular weights of >20,000, preferably 30,000 to 70,000, g/mol, most preferably about 50,000 g/mol. It is possible to use as matrix material for example a nonwoven made of polyglycolic acid as marketed by Alpha Research Switzerland GmbH under the brand name PGA-Soft Felt®.

This material is CE-certified and therefore suitable for pharmaceutical purposes. The absorption time for this product in vivo is about 40 to 60 days. After seven days in vitro, the mechanical strength as a consequence of hydrolysis is still about 50% of the initial value.

The cell-free graft of the invention includes a gel besides the matrix. This gel is applied to at least one side of the matrix, and/or at least partly penetrates the latter. The gel preferably penetrates the matrix completely. The matrix, itself preferably has a structure different from that of a gel. More rigid structures as explicitly mentioned above with the exception of gels are very particularly preferred. The gel accordingly preferably has less rigidity than the matrix. Nonwoven and felt structures into which a gel is introduced are most preferred.

The gel may be a natural or synthetic hydrogel. It preferably has less rigidity than the matrix. The gel can for example be selected from polysaccharides, polypeptides, hyaluronic acid, fibrin, collagen, alginate, agarose and chitosan, and salts, derivatives and mixtures thereof. Examples of suitable salts are alkali metal and alkaline earth metal salts of the gels mentioned. Most preference is given to hyaluronic acid or a hyaluronic acid derivative, in particular hyaluronic acid salts such as Na hyaluronate. As depicted in FIG. 1, in particular the use of hyaluronic acid in combination with a matrix of the invention shows particularly advantageous ratios of wet weight and dry weight and is therefore particularly suitable in the processing of the graft, the drying and/or storage.

It is possible by adding a particular amount of a physiologically suitable solution to adjust the hardness/strength of the transplant to the hardness of cartilage and/or bone, and the patient's tissue.

Types of hyaluronic acid which can be used are types produced by fermentation. An alternative possibility is also the use of hyaluronic acid obtained from animals. The average molecular weight of the types used is normally between 250 and 6000 kDa, preferably 1000 to 2000 kDa, most preferably about 1200 kDa. Suitable hyaluronic acid products are commercially available. The type of hyaluronic acid marketed under the brand name Ostenil® by TRB Chemedika AG is a suitable example. This material is CE-certified and therefore suitable for pharmaceutical purposes.

The gels can be formed by swelling, precipitation or polymerization of a suitable gel former in a physiologically suitable solution. Examples of such suitable solutions are water and aqueous solutions of salts (e.g. alkali metal and alkaline earth metal halides (Cl, Br, I), carbonates, phosphates, citrates, acetates and the like), organic acids, buffer substances and mixtures thereof. It is alternatively possible to use more complex solutions such as culture medium or body fluids or solutions derived therefrom, such as synovial fluid. The amount of gel former used is such that it provides an appropriate viscosity of the gel. For hyaluronic acid this is normally in the range 0.5-50 mg/ml, preferably 0.5-20 mg/ml, most preferably 10 mg/ml.

The most preferred graft is made of a polyglycolic acid (PGA) nonwoven or felt as matrix, into which a hyaluronic acid gel is incorporated.

The dimensions of the cell-free graft of the invention generally depend on the dimensions of the defect to be treated or the required size of the graft. The dimensions are to be adapted as required by the treating clinician. For lesions in cartilage tissue, especially in the knee joint, these sizes are normally in the range from 10 to 50 mm in length, 10 to 50 mm in width and 0.5 to 3 mm in thickness, preferably 10 to 30 mm in length, 10 to 30 mm in width and 1 to 2 mm thickness. The most preferred sizes are 20×30 mm in width and length and 1.1 to 2 mm in thickness. Appropriate dimensions can be adapted for non-square forms, e.g. rectangular, circular, oval, polyhedral, etc.

After the matrix has been contacted with the gel it can be dried. The drying of the implant of the invention allows on the one hand long-term storage and on the other easy use of the implant per se. Thus, the implant can be used after storage directly in the dry state or be again contacted with an aqueous solution.

The dried implant makes it possible easily to introduce aqueous solutions before use of the implant by a "sponge effect". The aqueous solution is sucked into the implant by simply being applied to the implant or by placing the implant in the aqueous solution. Physiological saline solution and/or synovial fluid is preferred for introducing an aqueous solution into the implant before use.

Suitable concentrations of the physiological saline solution and/or synovial fluid are 1 to 100% by volume of the volume of gel and fluid held by the matrix. The concentrations are preferably from 10 to 90%, more preferably 40 to 70% and most preferably 50% of the liquid volume held inter alia by capillary forces. To reduce the concentration of synovial fluid below 100% it is possible to employ synovial fluid diluted with aqueous solution. The synovial fluid is preferably diluted with physiological saline solution.

The use of the undried or dried cell-free implant of the invention without previous contacting with an aqueous solution for implantation in a defect makes it possible, through the concentration gradient present in the patient, for endogenous fluids—such as synovial fluid—to penetrate passively into the implant. The synovial fluid, with any messengers present in aqueous solution, which has penetrated thus into the implant increases the efficiency of the implant for recruiting mesenchymal progenitor cells from the bone marrow into the implant or the site of the defect.

The use of the cell-free undried or dried implant of the invention after contacting with physiological saline solution before the implantation for implantation in a defect makes it possible for a concentration gradient of messengers/endogenous substances in aqueous solution, such as growth and differentiation factors and/or chemokines, to be formed. In this way, endogenous messengers from the synovial fluid are introduced passively by diffusion into the cell-free implant, and increase the efficiency of the implant for recruiting mesenchymal progenitor cells from the bone marrow. The chemotactic effect of growth and differentiation factors such as, for example, cartilage derived morphogenetic protein 1 (CDMP1) or growth and differentiation factor 5 (GDF5) and cartilage derived morphogenetic protein 2 (CDMP2) or growth and differentiation factor 6 (GDF6) on mesenchymal stem and progenitor cells are described in DE 199 57 388. The chemotactic effect or the use of chemokines such as, for example, stromal derived factor 1α (SDF1-α) or interleukin-8 (IL8) for recruiting mesenchymal stem and progenitor cells is likewise described in DE 103 33 901. The chemotactic effect or the use of human serum for recruiting progenitor cells from bone marrow is disclosed in DE 10 2005 030 614. The test method for determining the chemotactic activity of substances is likewise disclosed in DE 10 2005 030 614.

Figure 3:
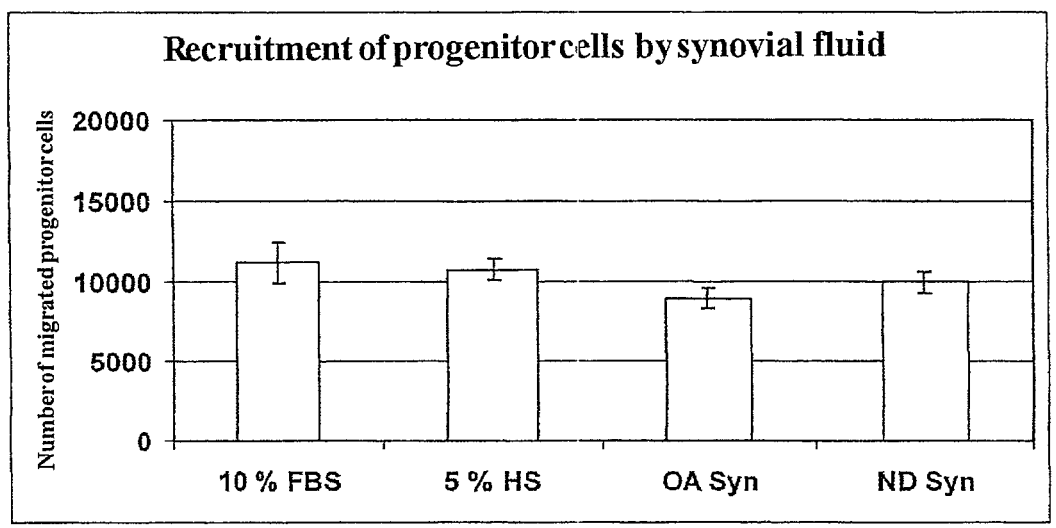
FIG. 3 shows the chemotactic effect (recruitment) of human synovial fluid on human mesenchymal stem cells in vitro. The abbreviation "FBS" means fetal bovine serum, "HS" stands for human serum. "OA Syn" is synovial fluid from patients with osteoarthrosis and "ND Syn" is synovial fluid from healthy donors (normal donors). The exact data underlying this figure are described in example 4.

Tests of the chemotactic effect of synovial fluid from normal donors and donors with osteoarthrosis for mesenchymal progenitor cells of the bone marrow in the test method described in FIG. 3 surprisingly revealed that human synovial fluid from healthy donors and from donors with osteoarthrosis recruits a comparable number of progenitor cells compared with serum. The cell counts of the mesenchymal progenitor cells recruited on average with corresponding standard deviations are depicted in FIG. 3. The results are compiled in example 4.

The use of synovial fluid in the cell-free implant of the invention surprisingly allowed the efficiency of recruitment of mesenchymal progenitor cells from the perfused bone marrow to be increased by several orders of magnitude by comparison with growth and differentiation factors (see FIG. 3). This surprisingly increased efficiency of recruitment makes it possible to dispense with the separate introduction of differentiated cells or progenitor cells in the graft itself. This makes handling of the graft much easier, and production of the graft simpler because no manipulation steps on the graft are necessary. Its production time is greatly shortened thereby, and production is cost-effective with comparable or just as good efficiency of recruitment.

It has surprisingly emerged that the efficiency of recruitment of synovial fluid corresponds to the efficiency of recruitment of blood serum. Synovial fluid is an integral constituent of the joint and can be obtained in a simple manner by conventional means. This can preferably take place, in the case of contacting before the implantation, directly during the implantation from the patient himself. It is thus possible to reimplant autologous material in the patient, while addition of other potentially allergenic and/or immunologically active factors is unnecessary. A second procedure to remove blood from the patient to obtain serum is avoided.

Since the migration of the cells and/or factors into the graft is made possible without the use of exogenous cells or the use of exogenous biological messengers, the risk of infection and allergenic risk for the patient is greatly minimized. It is additionally possible for this "simplified" graft of the invention to be dried and/or stored very readily. This makes it particularly cost-effective and user-friendly.

The combination of matrix and gel in the cell-free graft of the present invention also has the advantage that the gel forms a mechanical barrier to cells other than mesenchymal progenitor cells of the blood which penetrates in through the Pridie perforation or similar fractures. This makes it possible for mesenchymal progenitor cells to migrate selectively into the graft. It is therefore only they which establish themselves in the matrix and differentiate to the desired tissue cells. Overgrowth of the desired tissue-forming cells by other cells therefore does not take place or can be substantially diminished.

At the same time, the gel imparts through its viscosity a viscoelastic property on the implant, and thus the mechanical properties of the implant are approximated to the properties of the natural biomatrix of the cartilage. This approximation of the mechanical properties and the strength of the implant to the surrounding tissue is tolerable for the surrounding and, in the case of the joint, the opposing cartilage tissue and makes it possible for the joint to be load-bearing earlier after the patient has received the implant. In addition, the viscoelastic properties of the implant which are achieved through the viscosity of the gel protect the underlying tissue from mechanical impact and compressive stresses, which assist healing of the defect.

Since the moisture content of the matrix-gel graft can be adjusted specifically by drying before the implantation, it is possible to adapt the elasticity/hardness of the graft to the patient, so that the latter does not feel any foreign-body sensation after the implantation.

In addition, the cell-free graft of the invention makes it possible, because of the open porosity of the matrix, for the non-cellular components of the blood to penetrate in by diffusion, which makes efficient coagulation of the blood and thus hemostasis possible in the defect area after a microfracturing or Pridie perforation. The covering of the defect after micro-fracturing with the implant of the invention leads to hemostasis, which makes earlier healing of the defect possible.

The cell-free graft described above can be produced by a method in which the matrix is brought into contact with the gel. This contacting can take place by application dropwise, soaking, impregnation and/or steeping.

The method of the invention comprises a drying step. The use of a drying step has the advantage that the graft can be stored longer in dry form. If the dried cell-free graft is combined before use for implantation with an aqueous solution, such as physiological saline solution and/or synovial fluid, this can take place for example by steeping or soaking. It is then possible by the renewed contacting of the dried graft with an aqueous solution also simultaneously to adapt the elasticity/hardness of the graft individually to the patient.

The drying of the cell-free graft can take place by convection drying, air drying, vacuum drying, condensation drying, microwave drying, freeze drying, heat drying, chemical drying, or dielectric drying. The drying preferably takes place by freeze drying.

For the abovementioned preferred embodiment of polyglycolic acid nonwoven with hyaluronic acid gel, for nonwoven sizes of 20 mm×30 mm×1.1 mm approximately 600 µl of a hyaluronic acid solution (10 mg/ml) in a physiologically suitable solution is introduced into the material and dried by freeze drying. The dry cell-free implants can be moistened by steeping with 1 to 2 ml of solution. The steeping preferably takes place with physiological saline solution, with synovial fluid and/or with diluted synovial fluid.

The cell-free matrix-gel graft of the invention can be used to cover and increase the viscous elasticity of defects for tissue regeneration of mesenchymal tissues and in particular for regeneration of cartilage and/or bone. It is preferably used for regenerating mesenchymal tissue. Use for cartilage regeneration is most preferred, in particular after Pridie perforation or microfracturing. The implant acts as intelligent covering which, after a Pridie perforation or micro-fracturing, is introduced accurately fitting into the cartilage to restore the joint surface. The matrix material, preferably felt material, serves for mechanical stability and acts as lead structure which promotes homogeneous three-dimensional distribution of the patient's cells migrating in from the bone marrow or spongy bone, and has a hemostatic effect. The gel, such as, for example, hyaluronic acid, acts as barrier in order to prevent the migration in of red blood cells and leukocytes, and confers its viscoelastic properties on the implant, which protects the surrounding and underlying tissue from mechanical stress. The drying of the implant achieves a longer storability and makes it possible for endogenous synovial fluids or messengers to penetrate in passively. It has surprisingly emerged that the use of synovial fluid makes it possible for the recruitment numbers to be distinctly increased compared with the use of growth and differentiation factors, and chemokines and comparable recruitment numbers such as serum (see FIG. 3).

Having generally described this invention, a further understanding can be obtained by reference to certain specific examples which are provided herein for purposes of illustration only, and are not intended to be limiting unless otherwise specified.

EXAMPLES

Example 1

A commercially available polyglycolic acid nonwoven marketed under the brand name PGA-Soft Felt® by Alpha Research Switzerland GmbH was cut to the dimensions of 20 mm×30 mm×1.1 mm. The material was steeped with 0.6 ml of commercially available hyaluronic acid marketed under the brand name Ostenil® by TRB Chemedica AG, with a concentration of 10 mg/ml, with the aid of an automatic perfusor. The matrix-gel combination obtained in this way was dried with an Epsilon 2-6 LSC freeze dryer for about 17 hours. For this purpose, the gel-matrix combination was cooled from 20° C. to −20° C. in 90 minutes and left at −20° C. for 3 hours. As further drying step, a vacuum of 1.03 mbar was applied at −20° C. for 45 minutes. The matrix-gel graft was then heated from −20° C. to 20° C. in 2 hours at 1.03 mbar in order to dry at 20° C. and 1.03 mbar for a further 6.5 hours. In the last drying step, the temperature was raised to 25° C. and the pressure was reduced to 0.011 mbar over the course of 1 hour. After a further 2 hours at 25° C. and 0.011 mbar, the last drying step was complete.

The amount of displaced or dried liquid in the cell-free matrix-gel graft was established by determining the weight. The weight determined in each case is depicted in FIG. 1. On average, 0.6 ml of hyaluronic acid weighed 0.589 mg (HA). Soft PGA Felt® with a size of 20×30×1.1 mm weighed on average 0.155 mg (matrix). The wet weight of the matrix-gel combination before drying in the freeze drying was on average 0.744 mg (wet weight of HA+matrix). The dry weight of the matrix-gel combination after freeze drying was on average 0.166 mg (dry weight of HA+matrix). The weight of the liquid displaced from the matrix-gel combination by drying was on average 0.579 mg (displaced liquid).

After drying of the matrix-gel combination, the cell-free graft was ready for use/or storage.

Example 2

Figure 2:
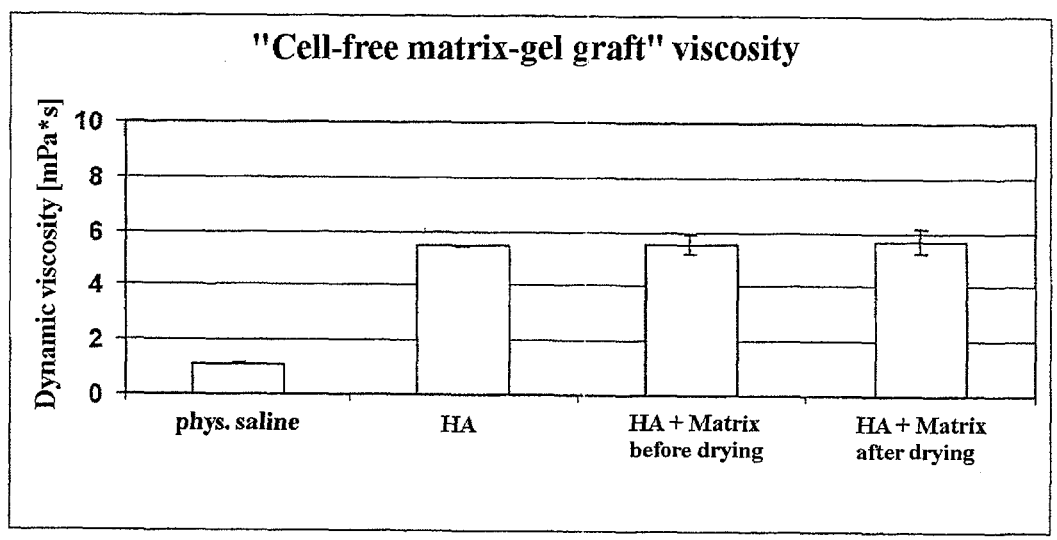
FIG. 2 shows the dynamic viscosity of hyaluronic acid and cell-free grafts before and after drying by lyophilization. The abbreviation "phys. saline" means physiological saline solution, "HA" means hyaluronic acid and "mPa*s" is the unit of dynamic viscosity in millipascal second. The exact design of the experiment underlying this figure is described in example 2.

A commercially available polyglycolic acid nonwoven marketed under the brand name PGA-Soft Felt® by Alpha Research Switzerland GmbH was cut to the dimensions of 20 mm×15 mm×1.1 mm. The material was steeped with 0.3 ml of commercially available hyaluronic acid marketed under the brand name (Ostenil® by TRB Chemedica AG, with a concentration of 10 mg/ml. The matrix-gel graft obtained in this way was dried in a freeze dryer for 17 hours. The retention of viscoelastic properties of the cell-free matrix-gel graft after freeze drying was shown by measuring the dynamic viscosity. The resulting viscosity measurements are shown in FIG. 2. To measure the dynamic viscosity, the dry cell-free matrix-gel graft was mixed with 0.3 ml of physiological saline solution and incubated at 4° C. while shaking gently for 16 hours. To obtain the rehydrogenated hyaluronic acid present in the graft, the graft was transferred into a pipette tip (1000 µl) standing in a reaction vessel and centrifuged at 2000 rpm for 10 minutes. The dynamic viscosity was measured in 1:10 dilution with physiological saline solution in an automatic AMVn microviscometer at 20° C.

For comparison, the dynamic viscosity of physiological saline solution, of the hyaluronic acid Ostenil® in 1:10 dilution with physiological saline solution and of the hyaluronic acid from the matrix-gel combination before freeze drying in 1:10 dilution with physiological saline solution was determined. The dynamic viscosity determined for the physiological saline solution was on average 1.09 mPa*s (phys. saline) and for the hyaluronic acid Ostenil® in 1:10 dilution with physiological saline solution was on average 5.48 mPa*s (HA). The dynamic viscosity of the hyaluronic acid in the matrix-gel combination before drying in the freeze dryer was on average 5.54 mPa*s (HA+matrix before drying). The dynamic viscosity of the hyaluronic acid in the cell-free graft after freeze drying was on average 5.69 mPa*s (HA+matrix after drying). This shows that the viscoelastic properties of the hyaluronic acid were not changed in the production process. After drying of the matrix-gel graft it was ready for use or storage.

Example 3

A polyglycolic acid nonwoven with the dimensions 20 mm×30 mm×1.1 mm was steeped with 0.6 ml of hyaluronic acid with a concentration of 10 mg/ml. The matrix-gel combination obtained in this way was dried in a freeze dryer as described in example 1.

For use, the dry cell-free matrix-gel graft was incubated in physiological saline solution for 5 minutes.

A defect of the articular cartilage of the knee undergoes arthroscopic cleaning and treatment by micro-fracturing by the usual method. The cell-free matrix-gel graft was introduced into the joint and used to cover the microfractured defect and for hemostasis. The covering in the defect can be fixed by bonding in with fibrin glue, by suturing the matrix to the surrounding articular cartilage (cartilage suture), by anchoring the matrix in the subchondral bone (transosseous fixing) or by fixing the matrix in the defect using absorbable pins or nails countersunk in the bone.

Example 4

Tests of the chemotactic effect of synovial fluid from normal donors and donors with osteoarthrosis for mesenchymal progenitor cells of the bone marrow surprisingly revealed that human synovial fluid from healthy donors and from donors with osteoarthrosis recruits a comparable number of progenitor cells compared with serum. The cell counts of the mesenchymal progenitor cells recruited on average with corresponding standard deviations are depicted in FIG. 3.

The use of 10% fetal bovine serum was able to stimulate on average 11 143 progenitor cells to migrate in vitro (10% FBS). 5% human serum stimulated on average 10 715 progenitor cells to migrate (5% HS). Synovial fluid from donors with osteoarthrosis in a 1:2 dilution with the cell culture medium DMEM stimulated on average 8907 cells, and synovial fluid from normal donors, likewise in 1:2 dilution in DMEM, stimulated on average 9920 progenitor cells to migrate.

DE 10 2005 030 614 states that the number of mesenchymal stem and progenitor cells recruited by the growth and differentiation factors CDMP1 and CDMP2 respectively does not exceed 156 and does not exceed 38 cells. It is further disclosed that the chemokine SDF1-α stimulated not more than 79, and the chemokine IL-8 stimulated not more than 814, cells per 25 $mm^2$ to migrate. Human serum stimulated between 2135 and 10 332 mesenchymal cells to migrate, depending on the formulation.

Example 5

A polyglycolic acid nonwoven with the dimensions 20 mm×30 mm×1.1 mm was steeped with 0.6 ml of hyaluronic acid with a concentration of 10 mg/ml. The matrix-gel graft obtained in this way was dried in a freeze dryer as described in example 1.

For use, the dry cell-free graft was steeped in autologous synovial fluid which was removed intra-operatively from the patient to be treated and was diluted in the ratio 1:2 with physiological saline solution for 10 minutes.

A defect of the articular cartilage of the knee undergoes arthroscopic cleaning and treatment by micro-fracturing by the usual method. The cell-free graft steeped in synovial fluid was introduced into the joint and used to cover the microfractured defect. The covering in the defect can be fixed by bonding in with fibrin glue, by suturing the matrix to the surrounding articular cartilage (cartilages suture), by anchoring the matrix in the subchondral bone (transosseous fixing) or by fixing the matrix in the defect using absorbable pins or nails countersunk in the bone.

German patent application 10 2006 047 346.9, filed Oct. 6, 2006 and International application PCT/EP2007/060384, filed Oct. 1, 2007, are incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A cell-free graft, comprising:
   (i) a cohesive, scaffold-forming matrix with open porosity comprising a biologically and pharmaceutically acceptable material;
   wherein the matrix has a structure selected from the group consisting of wovens, nonwoven structures, felt structures, wadding, wool, and combinations thereof; and
   wherein the matrix comprises a material selected from the group consisting of polyglycolic acid, polylactic acid, poly(glycolide, lactate), and mixtures thereof; and
   (ii) a hyaluronic acid gel wherein said gel is present on at least one side of the matrix, and wherein said gel penetrates the matrix at least partly.

2. The cell-free graft as claimed in claim 1, in which the matrix is absorbable.

3. The cell-free graft as claimed in claim 1, in which the gel is a natural or synthetic hydrogel.

4. The cell-free graft as claimed in claim 1, in which gel has been dried onto the matrix.

5. The cell-free graft as claimed in claim 4, wherein the drying of the gel takes place by convection drying, air drying, vacuum drying, condensation drying, microwave drying, freeze drying, heat drying, chemical drying, dielectric drying or a combination thereof.

6. The cell-free graft as claimed in claim 1, in which the matrix is polyglycolic acid.

7. The cell-free graft as claimed in claim 4, wherein the drying of the gel takes place by freeze drying.

8. A cell-free graft, consisting of:
   (i) a cohesive, scaffold-forming matrix with open porosity comprising a biologically and pharmaceutically acceptable material,
   wherein said matrix comprises a material selected from the group consisting of polyglycolic acid, polylactic acid, poly(glycolide, lactate), and mixtures thereof; and
   (ii) a hyaluronic acid gel,
   wherein the gel is present on at least one side of the matrix, and/or wherein the gel penetrates the matrix at least partly.

9. A method for producing a cell-free graft, comprising:
   (a) contacting a matrix with a gel, to obtain a matrix-gel complex; and
   (b) drying the matrix-gel complex formed in (v); to obtain said cell-free graft;
   wherein said matrix is a cohesive, scaffold-forming matrix with open porosity comprising a biologically and pharmaceutically acceptable material,
   wherein said matrix has a structure selected from the group consisting of wovens, nonwoven structures, felt structures, wadding, wool, and combination thereof; and
   wherein said matrix comprises a material selected from the group consisting of polyglycolic acid, polylactic acid, poly(glycolide, lactate), and mixtures thereof; and
   wherein said gel is a hyaluronic acid gel;

wherein said cell-free graft comprises
(i) said matrix; and
(ii) said gel, wherein the gel is present on at least one side of the matrix, and/or penetrates the matrix at least partly.

10. A method for covering and increasing the viscoelasticity of a defect, comprising:
contacting said defect with a cell-free graft as claimed in claim 1.

11. The method as claimed in claim 10, which comprises covering of a defect of mesenchymal tissue.

12. The method as claimed in claim 10, which comprises covering a defect of cartilage, bone or combinations thereof.

13. A method of tissue regeneration, comprising: contacting an area in need thereof with a cell-free graft as claimed in claim 1 to regenerate tissue.

14. The method as claimed in claim 13, which comprises regenerating cartilage, bone or combinations thereof.

\* \* \* \* \*